(12) United States Patent
Ladet et al.

(10) Patent No.: US 8,865,215 B2
(45) Date of Patent: Oct. 21, 2014

(54) MATRIX FOR TISSUE REPAIR

(75) Inventors: Sébastien Ladet, Lyons (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 248 days.

(21) Appl. No.: 13/124,276

(22) PCT Filed: Oct. 16, 2009

(86) PCT No.: PCT/IB2009/007468
§ 371 (c)(1),
(2), (4) Date: Jul. 12, 2011

(87) PCT Pub. No.: WO2010/043978
PCT Pub. Date: Apr. 22, 2010

(65) Prior Publication Data
US 2011/0320009 A1    Dec. 29, 2011

Related U.S. Application Data

(60) Provisional application No. 61/196,487, filed on Oct. 17, 2008.

(51) Int. Cl.
A61K 9/34        (2006.01)
A61F 2/02        (2006.01)
A61L 27/48       (2006.01)
A61L 27/56       (2006.01)

(52) U.S. Cl.
CPC *A61L 27/56* (2013.01); *A61L 27/48* (2013.01)
USPC ........................................ 424/485; 623/23.72

(58) Field of Classification Search
None
See application file for complete search history.

(56) References Cited

U.S. PATENT DOCUMENTS

| 4,606,337 A | * | 8/1986 | Zimmermann et al. ......... 602/48 |
| 4,931,546 A | * | 6/1990 | Tardy et al. .................... 530/356 |
| 5,166,187 A | | 11/1992 | Collombel et al. |
| 5,510,418 A | * | 4/1996 | Rhee et al. ..................... 525/54.2 |
| 5,830,493 A | | 11/1998 | Yokota et al. |
| 2004/0002055 A1 | | 1/2004 | Andre et al. |
| 2004/0258731 A1 | | 12/2004 | Shimoboji et al. |

FOREIGN PATENT DOCUMENTS

| EP | 0 486 294 | * | 5/1992 |
| WO | WO 2009/031047 | | 3/2009 |
| WO | WO 2009/156866 | | 12/2009 |

OTHER PUBLICATIONS

Chaplin, Martin., Water Structure and Science, (Apr. 7, 2013), pp. 1-8.*
About.com, Solution Definition, acessed Jan. 31, 2013, p. 1.*
International Search Report PCT/IB2009/007468 dated Apr. 19, 2010.
Wei Tan et al. "Evaluation of Nanostructured Composite Collagen-Chitosan Matrices for Tissue Engineering" Tissue Engineering, vol. 7m No. 2. 2001.

* cited by examiner

*Primary Examiner* — Scott Long
*Assistant Examiner* — Lyndsey Beckhardt

(57) ABSTRACT

Implants include a porous layer made from a composition including a compound wherein collagen is cross-linked to a glycosaminoglycan, the porous layer being optionally joined to a collagen film.

12 Claims, 3 Drawing Sheets

MATRIX FOR TISSUE REPAIR

CROSS-REFERENCE TO RELATED APPLICATIONS

This application is a U.S. National Stage Application filed under 35 U.S.C. §371(a) of International Application No. PCT/IB2009/007468 filed Oct. 16, 2009, which claims the benefit of and priority to U.S. Provisional Application Ser. No. 61/196,487 filed Oct. 17, 2008, the entire contents of which are incorporated by reference herein.

BACKGROUND

Repairing damaged meningeal membranes has largely focused on implants (known as dural substitutes) which are grafted over damaged dura mater and are designed to replace and/or regenerate the damaged tissue. Current dural substitutes based on collagen matrices provide a good bioresorbable and safe substitute, compared to xenograft or allograft implants. Nevertheless, dural substitutes based on collagen matrices have low watertight properties to prevent cerebrospinal fluid ("CSF") leakage, short persistence and low suture retention for use in infratentorial or spine areas. Synthetic dural substitutes usually show good mechanical and watertight properties, but generally are not absorbable, show a lack of conformability and are less easy to use since they always require suturing.

SUMMARY

The present implantable structures include a porous layer that serves as a matrix to support tissue regeneration while providing high suture retention and a controlled and desirable time of in vivo resorption. The porous matrix layer is composed at least of two natural polymers or derivatives which can self-crosslinked without the use of chemical agents as a cross-linker or as initiators of the crosslinking. In embodiments, this porous matrix is combined with a non porous layer resulting in an implant that is particularly suited to limit CSF leakage and prevent the adhesion between the brain and the neo dura. The present implants can be used as a substitute for and/or as a scaffold to regenerate any tissue, such as, for example dura mater in either supratentorial, infratentorial or spine locations.

An aspect of the invention is an implant for tissue repair or regeneration comprising a porous layer comprising a self-crosslinked compound of a functionalized collagen and a glycosaminoglycan. The glycosaminoglycan may be chitosan.

In embodiments, the glycosaminoglycan displays a degree of acetylation of about 1% to about 50%.

In embodiments the porous layer comprises a functionalized collagen self-crosslinked to a first glycosaminoglycan and to a second glycosaminoglycan, the first glycosaminoglycan having a first degree of acetylation and the second glycosaminoglycans having a second degree of acetylation different from the first degree of acetylation.

In embodiments the functionalized collagen is oxidized collagen.

In embodiments the functionalized collagen is denatured, oxidized collagen.

In embodiments the porous layer further comprises glycerine.

In embodiments the porous layer further comprises a bioactive agent.

In embodiments the porous layer has a thickness of from about 0.2 mm to about 1 cm.

In embodiments the porous layer comprises two or more sub-layers.

In embodiments a collagen film is joined to the porous layer.

Another aspect of the invention is a method of forming a porous layer suitable for implantation at the site of a tissue defect, the method comprising freeze-drying a composition comprising a self-crosslinked compound of a functionalized collagen and a glycosaminoglycan.

Another aspect of the invention is a method of forming a multi-layer structure suitable for implantation at the site of a tissue defect, the method comprising:

freeze-drying at least one composition comprising a self-crosslinked compound of a functionalized collagen and a glycosaminoglycan to provide a porous layer; and combining the porous layer with a collagen film to provide a multi-layer structure.

In embodiments, combining the porous layer with the collagen film comprises pouring a solution containing collagen onto a substrate;

allowing the solution to cool and partially gel;

contacting the porous layer with the partially gelled solution; and allowing the solution to completely gel to form the collagen film.

In embodiments, combining the porous layer with the collagen film comprises placing the porous layer onto a substrate;

pouring a solution containing collagen onto the porous layer;

allowing the solution to cool and gel to form the collagen film.

In embodiments, the step of freeze-drying at least one composition comprises freeze drying two juxtaposed compositions prepared by at least partially gelling a first solution; and applying a second solution directly onto the at least partially gelled first solution.

In embodiments, the step of freeze-drying at least one composition comprises freeze drying two juxtaposed compositions prepared by providing a layer of a first solution, the first solution having a first viscosity;

applying a layer of a second solution directly onto the layer of a first solution, the second solution having a viscosity lower than the viscosity of the first solution.

Another aspect of the invention is a method of treating a tissue defect comprising providing an implant as above and implanting the implant at the site of a tissue defect. In embodiments, the tissue defect is a defect in dura mater.

According to the present description, the expressions "porous layer" and "porous matrix" have the same meaning and both designate a porous layer. By "porous layer" is meant, according to the present description, a layer having pores, voids, holes, channels, favourable to cell colonization. For example, the porous layer may be a sponge or a foam.

By "non porous layer", is meant, according to the present description, a layer being substantially free of any pores and having a substantially even surface, not favourable to cell colonization. For example, the non porous layer may be a film.

DETAILED DESCRIPTION OF PREFERRED EMBODIMENTS

The present implants are fully bioresorbable and can include one or more layers. The present implant can be used in any procedures where the repair or substitution of a patient's tissue is needed or desired. In embodiments, the implant is used for the repair or substitution of a patient's dura mater. The implant is composed of glycosaminoglycans and collagen and/or its derivatives (such as, for example, oxidized collagen, gelatin and oxidized gelatin). In most preferred embodiments, the glycosaminoglycans are chitosan and derivatives.

Figure 1:
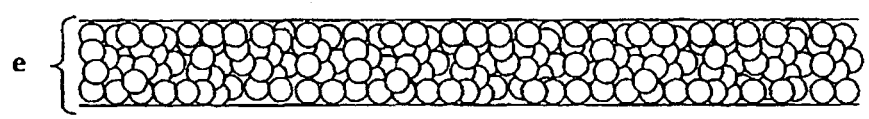
FIG. 1 schematically represents a monolayer implant in accordance with an embodiment of the present disclosure.

In embodiments, the present implant is a mono layered structure as seen in FIG. 1. In embodiments, this mono layered embodiment includes a porous layer made of chitosan and non heated, oxidized collagen. In embodiments, the porous layer persists at the site of implantation at least two weeks before being fully resorbed.

Figure 2:
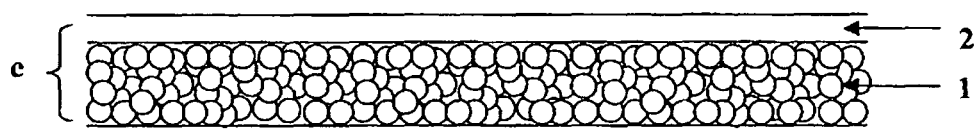
FIG. 2 schematically represents a two layer implant in accordance with an embodiment of the present disclosure.

In other embodiments, the present implant is a bi-layered structure as shown in FIG. 2. The first layer 1 is a biodegradable porous layer made of chitosan and oxidized collagen. In embodiments, the porous layer persists at the site of implantation at least two weeks before being fully resorbed. In embodiments, non-porous layer 2 is a biodegradable film based on collagen and/or its derivatives, PEG and glycerol. Non-porous layer 2 prevents adherences to the implant and minimizes the leakage of the cerebrospinal fluid. In embodiments, non-porous layer 2 persists at the site of implantation at least one week before being fully resorbed.

In use, the bi-layered implant is oriented with the non porous layer in contact with a tissue defect. Eventually, fluid will migrate through the non porous layer to allow the implant to conform to the defect. Alternatively, the implant can be hydrated before application to the tissue defect. In the dry state, when the implant is directly applied on the defect, the non porous layer can provide a sticky effect which provides an ease of use for the physician.

In embodiments, the present implants based on this self-crosslinked formulation provide better mechanical properties such as suture retention strength than equivalent implants based on purified collagen even where such collagen implants are cross-linked with chemical agents such as formaldehydes or glutaraldehyde. Moreover, the suture retention strength can be modulated according to the ratio of oxidized collagen and glycosaminoglycans. As used herein, the term "self-crosslinked" when used in connection with the crosslinking of polymers means that two or more polymers are covalently bonded together by functionalities present on the polymers themselves without the use of a chemical cross linking agent. As an illustrative example, oxidized collagen (which contains aldehyde groups thereon) will covalently bond to chitosan (which contains amino groups thereon) without the addition of any separate chemical crosslinking agent to form a self-crosslinked compound.

This ratio of oxidized collagen and glycosaminoglycans also provides the advantage of forming a tuneable in-vivo degradation profile allowing a wide range of implants with different in-vivo persistence. The in-vivo persistence of the implant can be advantageously managed by the degree of acetylation of the chitosan since chitosan provides different profiles of in-vivo persistence depending on the degree of acetylation.

In embodiments, the thickness (indicated by "e" in FIG. 1 and in FIG. 2) of the fully processed implant, in the dry state, is in the range of about 0.2 mm to about 1 cm.

Collagen and its Derivatives

Collagen is a naturally occurring protein exhibiting good biocompatibility. It is the major structural component of vertebrates, forming extracellular fibers or networks in practically every tissue of the body, including skin, bone, cartilage, and blood vessels. In medical devices, collagen provides a more physiological, isotropic environment that has been shown to promote the growth and function of different cell types, facilitating the rapid overgrowth of host tissue after implantation.

For the purpose of the present application, the term "collagen" is intended to mean any known collagen of porcine, bovine or human origin, including both natural or recombinant collagen, esterified collagen, for example methylated, ethylated or alternatively succinylated collagen, glycosylated collagen (e.g., collagen glycosylated with free amino saccharides/polysaccharides, collagen glycosylated with saccharides/polysaccharides comprising vicinal diols, collagen glycosylated with saccharides/polysaccharides comprising —$CH_x(NH_2)$—$CH_y(OH)$— chemical bonds), or one of its derivatives.

The term "gelatine" here includes commercial gelatine made of collagen which has been denatured by heating and in which the chains are at least partially hydrolyzed (molecular weight lower than 100 kDa).

The collagen used can be of human or animal origin. Some non-limiting examples include, type I porcine or bovine collagen, type I, type III or type IV human collagen or mixtures in any proportions of these types. In embodiments, the collagen or gelatine used is a porcine collagen.

The collagen can be functionalized by using any method known to those skilled in the art to provide pendant portions of the collagen with moieties which are capable of covalently bonding with the amino groups of a polymer such as collagen itself including its derivatives or modified glycosaminoglycan. Examples of such pendant moieties include aldehyde groups, sulfone groups, vinylsulfone groups, isocyanate groups, acid anhydride groups, epoxide groups, aziridine groups and episulfide groups. In addition, electrophilic groups such as —$CO_2N(COCH_2)_2$, —$CO_2N(COCH_2)_2$, —$CO_2H$, —$CHO$, —$CHOCH_2$, —$N=C=O$, —$SO_2CH=CH_2$, —$N(COCH)_2$, —$S$—$S$—$(C_5H_4N)$ may also be added to pendant chains of the collagen to allow covalent bonding to occur with the natural polymer showing amino group on their chains. Other suitable functional groups which may be added to collagen include groups of the following structures wherein X is Halogen and R is hydrogen or $C_1$ to $C_4$ alkyl:

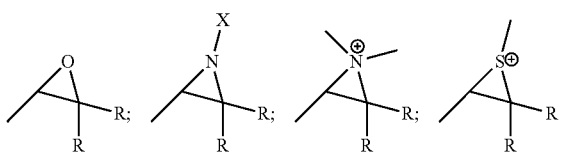

In embodiments, the collagen may be modified through the addition of an oxidizing agent. Contacting collagen with an oxidizing agent creates oxidative cleavage along portions of the collagen thereby creating pendant aldehyde groups capable of reacting with the glycosaminoglycans. The oxidizing agent may be, for example, iodine, peroxide, periodic acid, hydrogen peroxide, a periodate, a compound containing periodate, sodium periodate, a diisocyanate compound, a halogen, a compound containing halogen, n-bromosuccinimide, a permanganate, a compound containing permanganate, ozone, a compound containing ozone, chromic acid, sulfuryl chloride, a sulfoxide, a selenoxide, an oxidizing enzyme (oxidase) and combinations thereof. In embodiments, the oxidizing agent is periodic acid.

Oxidized collagen can be fully degraded in vivo, after few weeks. It is obtained by the oxidation of a 3% (w/w) collagen solution by periodic acid (C=8 mM) at room temperature, during 3 hours. An example of the oxidative technique is described by Tardy et al. in U.S. Pat. No. 4,931,546, the entire content of which is herein incorporated by reference. Another technique for oxidized collagen is by oxidation of a 3% collagen solution by periodic acid, at a final concentration of 8 mM, during 3 hours, as described in U.S. Pat. No. 6,596,304, the entire content of which is herein incorporated by reference.

Oxidation of collagen forms aldehydes groups which allow cross-linking of the collagen with the amino groups of the chitosan. The cross-linked blend chitosan/collagen is less prone to the enzymatic degradation and then has a longer time of bioresorption in-vivo. Moreover the covalent bonds generated by the cross-linking decrease the solubility of the material in water at physiological pH and allow the formation of a tri-dimensional network which is a support for cell growth and differentiation and then tissue regeneration.

Glycosaminoglycans and their Derivatives

The term "glycosaminoglycan" is intended to encompass complex polysaccharides having repeating units of either the same saccharide subunit or two or more different saccharide subunits. Some non-limiting examples of glycosaminoglycans include dermatan surfate, hyaluronic acid, the chondroitin sulfates, chitin, heparin, keratan surfate, keratosulfate, and derivatives thereof. Some non-limiting examples of derivatives may include partially and fully deacetylated versions of these compounds such as chitosan and deacetylated hyaluronic acid. The glycosaminoglycans may be extracted from a natural source, e.g., animal tissues such as squid pens and shrimp shells or vegetable sources such as mushrooms (e.g., "champignon de paris"), or they may be synthetically produced or synthesized by modified microorganisms such as bacteria.

In embodiments, the functionalized collagen may be combined with a glycosaminoglycan such as chitosan to crosslink and form covalent bonds. The glycosaminoglycan displays a degree of acetylation (DA) of about 0% to about 60%. In embodiments, the glycosaminoglycan displays a degree of acetylation (DA) of about 1% to about 50%. Samples of different degrees of acetylation can be obtained either by a heterogeneous deacetylation process or by a homogenous reacetylating process from a sample of a glycosaminoglycan that is fully deacetylated.

In embodiments, the glycosaminoglycan has a molecular weight ranging from about 100 to about 3,000,000 g/mol. In some embodiments, the glycosaminoglycan has a molecular weight ranging from about 179 to about 1,000,000 g/mol. In addition, the glycosaminoglycan also displays a low polydisperity index between about 1.1 to about 2. In particularly useful embodiments, the glycosaminoglycan is chitosan. Nevertheless, the glycosaminoglycan may be a mixture of chitosans with different degrees of acetylation or a mixture of chitosans and other glycosaminoglycans, e.g. deacetylated hyaluronic acid, with different degrees of acetylation and in which all glycosaminoglycan have the capability, i.e. have free amino groups, to be cross-linked to the oxidized collagen.

Porous Layer

The porous layer or matrix can be obtained by freeze-drying a polymer solution containing one or more biodegradable and biocompatible polymers. Table 1 shows illustrative embodiments of polymer solutions suitable for use in forming the porous layer using a free-drying process.

TABLE 1

| | |
|---|---|
| (A) chitosan content | 0.1%-99.9% (w/w) |
| (B) Oxidized collagen content | 99.9%-0.1% (w/w) |
| Total polymer concentration in the suspension | 0.2%-5% (w/w) |

Where both chitosan and collagen are used, the weight ratio of chitosan to collagen in the composition used to form the porous layer may be from about 1:100 to 100:1, in embodiments, the weight ratio of chitosan to collagen is from about 1:10 to about 10:1 in yet other embodiments, the weight ratio of chitosan to collagen is about 1:1.

In embodiments, the composition from which the porous layer is formed contains from about 40 to about 90 percent by weight chitosan and from about 10 to about 60 percent by weight functionalized collagen. In embodiments, the total polymer concentration in the suspension used to form the porous layer is from about 0.5% w/w to about 2% w/w.

Combining Collagen and Glycosaminoglycan to Form the Porous Layer

Compounds useful in forming the porous layer of the implant of the present disclosure can made by reacting a functionalized collagen with a glycosaminoglycan under conditions which cause the two components to form covalent bonds without the use of a chemical crosslinking agent. The two components may take the form of any solution, suspension, emulsion, semi-solid, or solid material capable of allowing the two-components to interact and self-crosslink.

In embodiments, each component is solubilized in an acceptable solvent such as deionized water to from two separate solutions. The two solutions may be combined to allow the two components to mix and self-crosslink to form the compounds described herein. In particular embodiments, the glycosaminoglycan is solubilized in deionized water with a stoechiometric amount of acid with a polymer concentration ranging from about 0.5% to about 10% (w/w). It is envisioned that the pH of the glycosaminoglycan solution can be adjusted if necessary between about 2 and about 7.5 depending on the degree of acetylation. The functionalized collagen is also solubilized in an acceptable solvent such as deionized water to a concentration ranging from about 0.5% to about 10% (w/w). It is also envisioned that the pH of the functionalized collagen solution may be adjusted between about 2 and about 7.5. The two components in solution are mixed to a final concentration of polymer comprising 0.5% and 20% (w/w). In embodiments, different proportions between the functionalized collagen and the glycosaminoglycan may be used. In particular embodiments, the glycosaminoglycan may be composed of a mixture of chitosans with different degrees of acetylation (DA). The chitosan having a degradation time in function with its degree of acetylation (Kurita et al., Carbohydrate polymers. Vol 42 pp. 19-21, 2000; Tomihata et al., Biomaterials. Vol 18 n° 7 pp. 567-575, 1997), the combination of slow and fast biodegradable chitosan is advantageous, for example, for progressive cell colonization of the porous layer. In fact, the degradation of the slow biodegradable oxidized collagen and chitosan with high DA, i.e. 35≤DA≤50, in vitro in the presence of viable cells and in vivo, helps to increase the interconnected porosity assisting in the regeneration of healthy native like tissue in the full thickness of the implant and the extent of tissue integration. Moreover the proportion of oxidized collagen and chitosan used to prepare the material is an important factor since chitosan and collagen have very different in-vivo degradation profiles. This allows the preparation of various implants having a tuneable in-vivo degradation profile. In embodiments, molecules released from the controlled degradation of the biocomposite, for example oxidized collagen/chitosan, may advantageously confer to the implant highly interesting biological activities e.g. antimicrobial, anticancer, antioxidant, and immunostimulant effects, especially in the case of chitosan (Kim et al., Carbohydrate Polymers, Vol. 62, Issue 4, pp. 357-368, 2005) and may bring, in complement of the biocompatibility and biodegradability, bioactive properties to the medical devices. The biological properties of released chitosan oligopolymers enhance the tissue regeneration and extend the use of the implant, for example, to surgical sites with a high risk of contamination.

In embodiments, a combination of two solutions comprising an acidic solution of oxidized collagen and an acidic solution of chitosan with one or a mixture of several degrees of acetylation. Using a mixture of chitosans having several degrees of acetylation allows the preparation of material having a profile of in-vivo degradation which can be tailored to the particular needs of a given application. The collagen is oxidized by the addition of periodic acid as the oxidizing agent and the chitosan solution is made acidic by the addition of hydrochloric acid. The mixture can be neutralized either with an alkaline vapour/solution or buffer solution with a pH greater than 7, leading to a cross-linked scaffold compatible for cell adhesion and proliferation.

Optionally, glycerine may be added to the solution used to form the porous layer. When present, the concentration of glycerine in the solution can typically be from about 2 to about 10 times less than that of the combined amount of collagen and glycosaminoglycan, in embodiments, less than about one-third of the combined amount of collagen and glycosaminoglycan.

Because of the polyelectrolyte characteristic of the natural polymers used to prepare the present implants, in embodiments it may be advantageous to add salt such as NaCl, in order to manage the viscosity of the blend before the step of freeze-drying.

The porous layer can from about 0.1 mm to about 10 mm thick in the dry state. In multi-layer embodiments, the porous layer can be from about 0.2 mm to about 5 mm thick in the dry state. The porous layer displaying such a thickness can have a density of from about 0.1 mg polymers (e.g., collagen and glycosaminoglycans) for each square centimetre (length× width of the porous layer) to about 50 mg polymers for each square centimetre, in embodiments from about 0.25 mg polymers for each square centimetre to about 20 mg polymers for each square centimetre. The size of the pores in such a porous layer can be from about 10 μm to about 1000 μm, in embodiments from about 50 μm to about 500 μm.

The porous matrix can be further compacted by using a press or any other appropriate means, so as to obtain a thickness comprised between 0.1 mm and 3 mm, in embodiments between 0.1 mm and 1 mm.

The Non-Porous Layer

Non porous layer suitable for use in the implants of the present disclosure can be a collagen film. Suitable collagen films can be made from non heated oxidized collagen, heated oxidized collagen, non oxidized heated collagen or combinations thereof. If heated oxidized collagen is used, the formulation of the film can be the formulations disclosed in U.S. Pat. No. 6,596,304, the entire disclosure of which is incorporated herein by reference.

Any bioactive agents which may enhance tissue repair, limit the risk of sepsis and any chemical additives which may modulate the mechanical properties (e.g., glycerol, 1-2 propandiol) of the film (swelling rate in water, tensile strength and the like) may be added during the preparation or in the film formulation.

The film may be further cross-linked by any known methods, when dried or during its drying.

Table 2 gives illustrative concentrations of collagen solutions useful in forming the non-porous layer.

TABLE 2

| Non heated oxidized collagen content | 0.1%-3% (w/w) |
| --- | --- |
| Heated Oxidized collagen content | 0.1%-6% (w/w) |
| Heated collagen content | 0.1%-6% (w/w) |

In embodiments, at least one macromolecular hydrophilic additive that is chemically unreactive with the collagen may be added to the solution used to form the non-porous layer. "Chemically unreactive with the collagen" as used herein means a hydrophilic compound which is not likely to react with the collagen, notably which does not form covalent bonds with it during cross-linking.

The macromolecular hydrophilic additive advantageously has a molecular weight in excess of 3,000 Daltons, in embodiments from about 3,000 to about 20,000 Daltons. Illustrative examples of suitable macromolecular hydrophilic additives include polyalkylene glycols (such as polyethylene glycol), polysaccharides (e.g., starch, dextran and/or cellulose), oxidized polysaccharides, and mucopolysaccharides. It should of course be understood that combinations of macromolecular hydrophilic additives may be used. The concentration of hydrophilic additive(s) can typically be from about 2 to about 10 times less than that of the collagen.

Typically, the macromolecular hydrophilic additive is eliminated by diffusion through the non-porous layer, in a few days. The swelling of this material may advantageously promote degradation of a collagenic non-porous layer in less than about one month.

Optionally, glycerine may be added to the solution used to form the non-porous layer. When present, the concentration of glycerine in the solution can typically be from about 2 to about 10 times less than that of the collagenic constituent, in embodiments less than about one-third of the collagen concentration.

The non-porous layer may be prepared by pouring a collagen-containing solution onto a substantially flat support and distributing it evenly. This solution is left to gel by the removal of solvent and cooling.

Examples of solutions useful in forming the non-porous layer include from about 0.1 to about 3% w/w of non-heated oxidised collagen, up to 2% w/w polyethylene glycol and up to 1% w/w glycerol. In embodiments, solutions useful in forming the non-porous layer include from about 0.5 to about 1.5% w/w of non-heated oxidised collagen, from about 0.6 to about 0.9% w/w polyethylene glycol and from about 0.3 to about 0.6% w/w glycerol.

In the dry state, the resulting non-porous layer may contain from about 40 to about 100% w/w of non-heated oxidised collagen, up to 60% w/w polyethylene glycol and up to 20% w/w glycerol. In embodiments, the resulting non-porous layer contains from about 60 to about 90% w/w of non-heated oxidised collagen, from about 15 to about 30% w/w polyethylene glycol and from about 5 to about 15% w/w glycerol.

Other examples of solutions useful in forming the non-porous layer include from about 0.1 to about 3% w/w of heated oxidised collagen, from about 0.1 to about 3% w/w of heated collagen, up to 2% w/w polyethylene glycol and up to 1% w/w glycerol. In embodiments, solutions useful in forming the non-porous layer include from about 0.5 to about 1.5% w/w of non-heated oxidised collagen, from about 0.5 to about 1.5% w/w of heated collagen, from about 0.6 to about 0.9% w/w polyethylene glycol and from about 0.3 to about 0.6% w/w glycerol.

In the dry state, the resulting non-porous layer may contain from about 40 to about 100% w/w of heated oxidised collagen, about 40 to about 100% w/w of heated collagen, up to 60% w/w polyethylene glycol and up to 20% w/w glycerol. In embodiments, the resulting non-porous layer contains from about 60 to about 90% w/w of heated oxidised collagen, from about 60 to about 90% w/w of heated collagen, from about 15 to about 30% w/w polyethylene glycol and from about 5 to about 15% w/w glycerol.

The thickness of the non-porous layer is not critical, but typically can be less than about 100 μm thick, and in embodiments from about 15 μm to about 75 μm thick, in a dry state.

Optional Bioactive Agents

In some embodiments, at least one bioactive agent may be combined with the present dural repair materials and/or any of the individual components (the porous layer or the optional non-porous layer) used to construct the present dural repair materials. In these embodiments, the present dural repair material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present dural repair materials in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive agents can be used to prevent adhesions from forming between the present dural repair materials and the surrounding tissues opposite the target tissue. In addition, anti-adhesive agents may be used to prevent adhesions from forming between the present dural repair materials and the packaging material. Some examples of these agents include, but are not limited to poly(vinyl pyrrolidone), carboxymethyl cellulose, hyaluronic acid, polyethylene oxide, poly vinyl alcohols and combinations thereof.

Suitable antimicrobial agents which may be included as a bioactive agent in the dural repair materials of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B and antimicrobial polysaccharides such as fucans and derivatives may be included as a bioactive agent in the dural repair materials of the present disclosure.

Other bioactive agents which may be included as a bioactive agent in the dural repair materials in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present dural repair materials include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ((3-IFN, (a-IFN and y-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Assembling the Multi-Layer Embodiments

When the implants described herein is a multilayer structure, the implant may be formed using any method known to those skilled in the art capable of connecting a non-porous layer to a porous layer. It is envisioned that the non-porous layer and the porous layer may be adhered to one another using chemical bonding, surgical adhesives, surgical sealants, and surgical glues. In addition, the layers may be bound together using mechanic means such as pins, rods, screws, clips, etc. Still further, the layers may naturally or through chemical or photoinitiation may interact and crosslink or provide covalent bonding between the layers.

In embodiments, the multilayer materials described herein are prepared by attaching the individual layers of materials together to form a multiple layer implant. The porous layer may be formed separate and apart from the non-porous layer. Alternatively, the porous and non-porous layers may be formed together.

In an illustrative embodiment, the present implants are prepared by first pouring a solution destined to form the film onto an adequate, substantially flat support and distributing it evenly.

The support is inert in that it does not react with the solution or its constituents. The support may advantageously be made from a hydrophobic material such as, for example, PVC or polystyrene. However, this support can also consist of a strippable material which will remain slightly adhesive and which can then be separated from the implant at the time of surgical use. This support may itself also consist of a film, for example dried collagen, onto which the solution is poured, or a layer of collagenic material gel in a distinctly more advanced state of gelification.

The density of the thin layer initially applied as a solution to the substrate can be from about 0.1 g solution/$cm^2$ to about 0.3 g solution/$cm^2$. This solution advantageously may be poured at a temperature from about 4° C. to about 30° C., and in embodiments from about 18° C. to about 25° C. Once applied to the substrate, the solution is allowed to partially gel. Partial gelling results from cooling of the solution, and not from drying of the solution.

This solution is left to gel and a porous layer previously prepared can be applied to the solution during gelification.

Application of the porous layer onto the solution during gelification means simply laying the porous layer onto the gel, and optionally applying slight pressing. The pressing should be insufficient to cause any significant compaction of the porous layer. In embodiments where the porous layer has been pre-formed, the porous layer will become joined to the solution, but will not become interlocked with the mesh reinforcement member.

The moment at which the porous layer is applied to the solution during gelification will depend upon the nature of the solution employed, the conditions under which the solution is maintained during gelification and the nature of the porous layer. Generally, the solution will allowed to gellify for a period of time prior to application of the porous layer such that the gel is still soft and allows the porous layer to penetrate over a distance which is advantageously from about 0.05 mm to about 2 mm and, in embodiments from about around 0.1 mm to about 0.5 mm. The appropriate moment for application of the porous layer for any given combination of materials/conditions can be determined empirically, for example by applying small samples of the porous layer to the gel at various times and evaluating the degree of penetration and adherence. Generally, when the solution which is gelling is at a temperature of between 4 and 30° C., the porous layer can be applied 5 to 30 minutes after the solution has been poured over the surface holding it.

The composite implant is left to dry or dried in order to obtain the final implant. When the solution destined to form the film includes oxidized collagen, it is polymerized while the material is drying. This drying occurs favorably at a temperature of from about 4° C. to about 30° C., in embodiments from about 18° C. to about 25° C. The material can be dried in a jet of sterile air if desired.

After drying, the implant can be separated from its support, packaged and sterilized using conventional techniques, e.g., irradiation with beta (electronic irradiation) or gamma (irradiation using radioactive cobalt) rays.

The present implants are stable at ambient temperature and remains stable for long enough to be handled at temperatures which may rise to 37-40° C. The dural repair materials in accordance with this disclosure can be produced at a desired size or produced in large sheets and cut to sizes appropriate for the envisaged application.

The present implants may be implanted using open surgery or in a laparoscopic procedure. When implanted laparoscopically, the present implants should be rolled with the porous side on the inside before trocar insertion.

The following non-limiting example illustrates the preparation of implants in accordance with the present disclosure.

EXAMPLES

Example 1

A compressed chitosan/collagen porous layer useful as a mono-layer implant or as part of a multi-layer implant is prepared as follows: 60.5 g of chitosan solution (DA 2.5%) and 60.5 g of non heated, oxidized collagen solution (1% w/w) are mixed at pH 3.5. The pH of the solution is adjusted to 4.5 and the blend is centrifuged. The solution is poured in 12×17 cm box and freeze-dried for 24 hours. The collagen sponges are compressed to obtain a thickness between of 0.1 and 1 mm. Then, the sponge is neutralized in 1M NaOH solution for 20 minutes. After a complete wash in sterile water until the pH is neutral, the sponge is freeze dried again to provide the porous layer of the implant.

Example 2

A compressed chitosan/collagen porous layer useful as a mono-layer implant or as part of a multi-layer implant is prepared using chitosans having different degrees of acetylation as follows: 20 g of chitosan solution (DA 2.5%), 40.5 g of chitosan solution (DA 38%), and 60.5 g of non heated, oxidized collagen solution (1% w/w) are mixed at pH 3.5. 1.21 g of glycerol is added to the solution under stirring for 10 minutes. The pH of the solution is adjusted to 4.5 and the blend is centrifuged. The solution is poured in 12×17 cm box and freeze-dried for 24 hours. The collagen sponges are compressed to obtain a thickness between of 0.1 and 1 mm. Then, sponge is neutralized in 1M NaOH solution for 20 minutes. After a complete wash in sterile water until the pH reaches 7, the sponge is freeze dried again to provide the porous layer of the implant.

Example 3

A compressed chitosan/collagen porous layer useful as a mono-layer implant or as part of a multi-layer implant is prepared as follows: 121 g of chitosan solution (DA 2.5%) and 121 g of non heated, oxidized collagen solution (1% w/w) are mixed at pH 3.5. 1.21 g of glycerol is added to the solution under stirring for 10 minutes. The pH of the solution is adjusted to 4.5 and the blend is centrifuged. 244.4 g of solution is poured in a 12×17 cm box and let under evaporation in a ventilated oven at 34° C.±3° C. for approximately 10 hours, until the final weight of the solution is 120±15 g. At this step the total amount of polymer in the solution is around 2%. Finally, the concentrate solution obtained is freeze-dried for approximately 24 hours. The sponge is compressed to obtain a thickness between of 0.1 and 1 mm. Then, it is neutralized in 1M NaOH solution for 20 minutes. After a complete wash in sterile water until the pH reaches 7, the sponge is freeze dried again to provide the porous layer of the implant.

Example 4

A compressed chitosan/collagen porous layer useful as a mono-layer implant or as part of a multi-layer implant is prepared as follows: 8.47 g of chitosan is dispersed in 76.3 g of water. The suspension of chitosan is then mixed with 36.3 g of non heated, oxidized collagen solution and 1.21 g of glycerol. The pH is adjusted close to a neutral pH and the blend is left under stirring for 1 hour under reduced pressure. The final mixture is poured in 12×17 cm box and freeze-dried for approximately 24 hours to provide the porous layer of the implant.

Example 5

A solution of heated, oxidized collagen suitable for forming the non-porous layer of the present implant is prepared as follows: To a 3.9% heated oxidized collagen solution, an ultra-filtered concentrated solution of PEG 4000 (polyethylene glycol having a molecular weight of 4000 g/mol) and glycerol is added, in order to achieve a PEG concentration of 1% and a glycerol concentration of 0.6%. The pH of the solution is adjusted to 7.0 by adding concentrate sodium hydroxide solution. The volume of the solution is then adjusted with sterile water to obtain final concentrations of collagen, PEG and glycerol of 2.7%, 0.9% and 0.54%, respectively.

Example 6

A solution suitable for forming the non-porous layer of the present implant is prepared as follows: To a 3.9% oxidized collagen solution, an ultra-filtered concentrated solution of PEG 4000 (polyethylene glycol having a molecular weight of 4000 g/mol) and glycerol is added, in order to achieve a PEG concentration of 1% and a glycerol concentration of 0.6%. To the solution is added one part of chitosan (DA=30%) for 20 parts of oxidized collagen by weight. The pH of the suspension is adjusted to 7.0 by adding concentrate sodium hydroxide solution. The volume of the solution is then adjusted with sterile water to obtain final concentrations of collagen, chitosan, PEG and glycerol of 2.7%, 0.13%, 0.9% and 0.54%, respectively.

Example 7

A solution suitable for forming the non-porous layer of the present implant is prepared as follows: To a 3.9% oxidized collagen solution, an ultra-filtered concentrated solution of PEG 4000 (polyethylene glycol having a molecular weight of 4000 g/mol) and glycerol is added, in order to achieve a PEG concentration of 1% and a glycerol concentration of 0.6%. To the solution is added one part of chitosan (DA=30%) for 5 parts of oxidized collagen by weight. The pH of the suspension is adjusted to a neutral pH by adding concentrate sodium hydroxide solution. The volume of the solution is then adjusted with sterile water to obtain final concentrations of collagen, chitosan, PEG and glycerol of 2.7%, 0.55%, 0.9% and 0.54%, respectively.

Example 8

A multi-layer implant is prepared as follows: The oxidized collagen solution of Example 5 is poured in a thin layer on a flat hydrophobic support of the PVC or polystyrene type, with a density of 0.133 g solution/cm$^2$. The surfaces are then exposed to a sterile stream of air at ambient temperature, during less than half of an hour. The compacted sponge is then gently applied on the gelling layer of oxidized collagen and the two layers are exposed to a sterile stream of air at ambient temperature. The two layers composite is exposed to a sterile stream of air at ambient temperature, leading to complete evaporation in at least approximately 18 hours.

Example 9

A multi-layer implant is prepared as follows: The compressed sponge is placed on a flat hydrophobic support of the PVC or polystyrene type. The oxidized collagen solution of Example 5 is poured over the compacted sponge, with a density of 0.295 g solution/cm$^2$. The two layers composite is exposed to a sterile stream of air at ambient temperature, leading to complete evaporation in at least approximately 20 hours.

Example 10

The following method may be used to prepare a sub-layered porous matrix for use in preparing a mono-layer implant or as part of a multi-layer implant in accordance with the present disclosure: A composition destined to form a first sublayer is prepared with a polymer concentration C1. This composition is poured into a container. A second solution destined to form the second sublayer is prepared having a polymer concentration C2 which is lower than concentration C1. This second solution is poured over the first solution layer. The difference of viscosity of the two solutions avoids the mixing of the two different layers to preserve to bi-layered structure. The two sublayers of the porous matrix are simultaneously freeze dried to provide a sub-layered porous matrix layer. If necessary, the porous matrix layer may be neutralized using a basic solution/vapour or buffer solution in order that the dissociation state of the first hydrogel precursor will be adapted for optimal reactivity with the second hydrogel precursor.

The sub-layered porous matrix produced can be used alone as a monolayer implant or cam be combined with a non-porous layer, for example as described above in Examples 8 and 9 to make a multi-layer implant.

Example 11

The following method may be used to prepare a sub-layered porous matrix for use in as a mono-layer implant or as part of a multi-layer implant in accordance with the present disclosure: 40.5 g of chitosan solution (DA 2.5%) and 40.5 g of non heated, oxidized collagen (also referred herein as CXN) solution (1% w/w) are mixed at pH 3.5 under stirring for 10 minutes. The pH of the solution is adjusted to 4.5. Finally the solution is centrifuged. The solution is poured in box and is destined to form one of the sublayers.

Then, 20 g of chitosan solution (DA 2.5%) and 20 g of CXN solution (0.5% w/w) are mixed at pH 3.5. This lower concentration solution is gently applied over the first sublayer and the whole is lyophilized as described above. The total lyophilization time is from 18 to 72 hours.

Then the porous matrix is neutralized within water/alcohol mixture 5/95 w/w with sodium hydroxyde 0.5N for 5 min and freeze dry again.

The sub-layered porous matrix produced can be used alone as a monolayer implant or cam be combined with a non-porous layer, for example as described above in Examples 8 and 9 to make a multi-layer implant.

Example 12

Figure 3A:
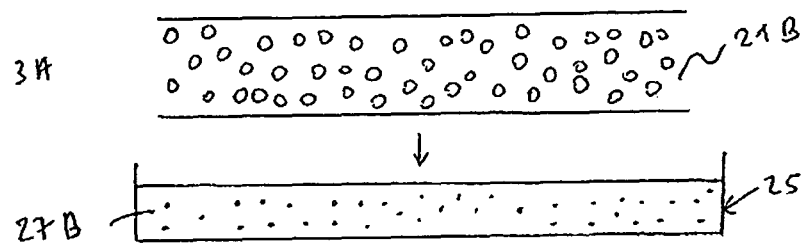
FIGS. 3A through 3C schematically illustrate a method of forming an implant in accordance with yet another embodiment of the present disclosure.
Figure 3B:
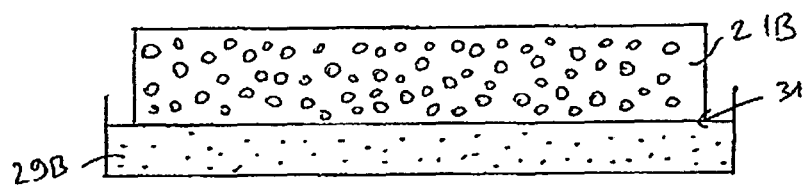
Figure 3C:
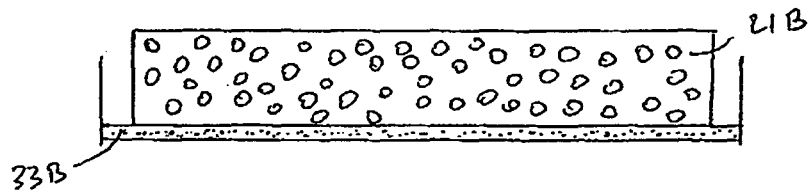

The following method may be used to prepare a multi-layer implant in accordance with the present disclosure: Referring to FIGS. 3A-3C, a sequence is shown wherein a pre-formed porous matrix layer 21B (which may or may not be sub-layered as described above) is applied to a gelling layer 29B formed from a solution layer 27B. Before the spreading of the solution 27B the pH is adjusted around 7.4. During a solvent casting step, porous layer 21B is at least partially impregnated of 29B forming a transition layer 31. After complete drying of gelling layer 29B, porous layer 21B and non-porous layer 33B are well associated.

Example 13

Figure 4A:
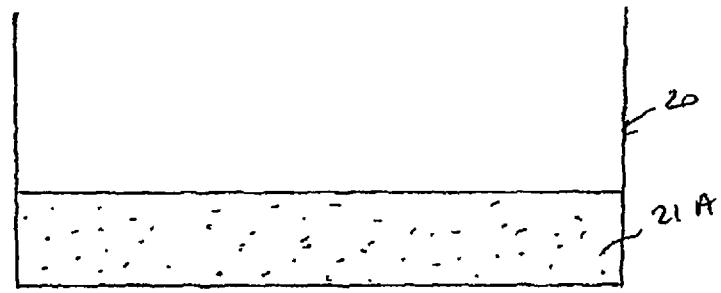
FIGS. 4A through 4D schematically illustrate a method of forming an implant in accordance with yet another embodiment of the present disclosure.
Figure 4B:
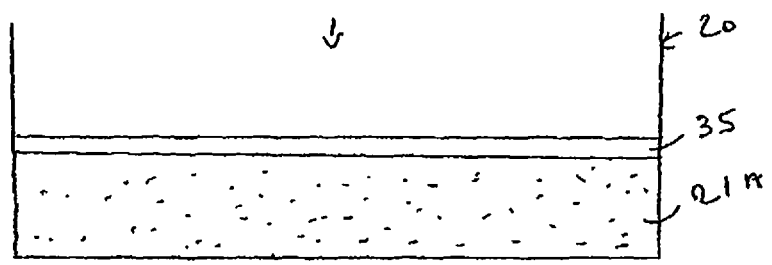
Figure 4C:
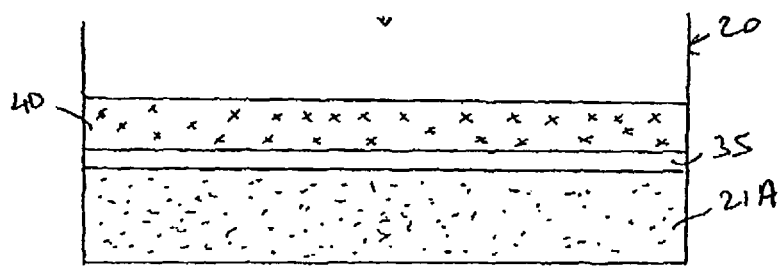
Figure 4D:
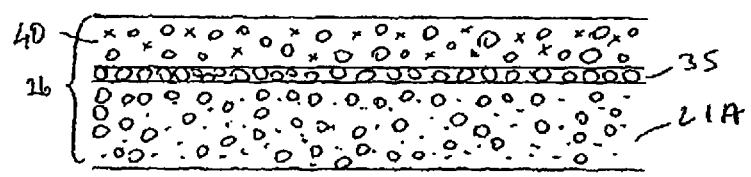

The following method may be used to prepare a multi-layer implant in accordance with the present disclosure: Referring to FIGS. 4A-4D, the steps for making a structure wherein a first polymer solution, with a polymer concentration C1, forms a first sublayer 21A of the porous matrix 26 in the container 20. Preferably, the pH of the polymer solution should be adjusted between 7 and 8. In FIG. 4B, a second solution 35, with a polymer concentration C2 different than C1, is poured over the first solution layer 21A which has been beforehand at least partially gelated or frozen. In FIG. 4C, a third solution 40 having a polymer concentration C3 is poured over solution layer 35 which has been beforehand at least partially gelated or frozen. Then, the three sublayers 26 of the porous matrix are freeze dried as shown in FIG. 4D.

It will be understood that various modifications may be made to the embodiments disclosed herein. Thus, those skilled in the art will envision other modifications within the scope and spirit of the claims.

The invention claimed is:

1. A method of forming a porous layer suitable for implantation at the site of a tissue defect, the method comprising freeze-drying a composition comprising a self-crosslinked compound of a functionalized collagen and a glycosaminoglycan, wherein the step of freeze-drying the composition comprises freeze drying two juxtaposed compositions prepared by providing a first sublayer of a first liquid solution, the first liquid solution having a first viscosity; and, applying a second sublayer of a second solution directly onto the first sublayer of the first liquid solution, the second solution having a second viscosity lower than the first viscosity of the first liquid solution.

2. A method as in claim 1 further comprising combining the porous layer with a collagen film to provide a multi-layer structure.

3. A method as in claim 2 wherein combining the porous layer with the collagen film comprises pouring a solution containing collagen onto a substrate; allowing the solution to cool and partially gel; contacting the porous layer with the partially gelled solution; and allowing the solution to completely gel to form the collagen film.

4. A method as in claim 2 wherein combining the porous layer with the collagen film comprises placing the porous layer onto a substrate; pouring a solution containing collagen onto the porous layer; allowing the solution to cool and gel to form the collagen film.

5. The method of claim 1 wherein the difference in viscosity of the first and second solutions avoids the mixing of the first and second sublayers.

6. The method of claim 1 wherein the first and second sublayers are simultaneously freeze-dried.

7. The method of claim 1 wherein the first liquid solution further comprises a first polymer concentration and the second solution further comprises a second polymer concentration, wherein the second polymer concentration of the second solution is lower than the first polymer concentration of the first liquid solution.

8. The method of claim 1 wherein the glycosaminoglycan is chitosan.

9. The method of claim 8 wherein the chitosan comprises a degree of acetylation of about 1% to about 50%.

10. The method of claim 1 wherein the functionalized collagen comprises oxidized collagen.

11. The method of claim 1 wherein the first liquid solution and the second solution are acidic solutions prior to freeze-drying.

12. The method of claim 11 wherein the porous layer is neutralized after freeze-drying.

* * * * *